United States Patent
Kelly

(10) Patent No.: US 7,906,554 B2
(45) Date of Patent: Mar. 15, 2011

(54) COMBINATION CHEMOTHERAPY COMPOSITIONS AND METHODS

(75) Inventor: Graham Edmund Kelly, Northbridge (AU)

(73) Assignee: Novogen Research Pty Ltd, North Ryde (AU)

( * ) Notice: Subject to any disclaimer, the term of this patent is extended or adjusted under 35 U.S.C. 154(b) by 322 days.

(21) Appl. No.: 10/530,176

(22) PCT Filed: Oct. 2, 2003

(86) PCT No.: PCT/AU03/01296
§ 371 (c)(1),
(2), (4) Date: Mar. 9, 2006

(87) PCT Pub. No.: WO2004/030662
PCT Pub. Date: Apr. 15, 2004

(65) Prior Publication Data
US 2006/0183728 A1   Aug. 17, 2006

(30) Foreign Application Priority Data

Oct. 2, 2002 (AU) ................................ 2002951833

(51) Int. Cl.
| | |
|---|---|
| A61K 33/24 | (2006.01) |
| A61K 31/55 | (2006.01) |
| A61K 31/35 | (2006.01) |
| A61K 31/28 | (2006.01) |
| A01N 43/54 | (2006.01) |
| A01N 43/02 | (2006.01) |
| A01N 55/02 | (2006.01) |

(52) U.S. Cl. ......... 514/456; 424/649; 514/274; 514/449; 514/492

(58) Field of Classification Search ................... 424/649; 514/274, 449, 456, 492
See application file for complete search history.

(56) References Cited

U.S. PATENT DOCUMENTS 6,380,405 B1 * 4/2002 Ekwuribe et al. ............. 549/510

FOREIGN PATENT DOCUMENTS

| CA | 2337256 A1 | 1/2000 |
|---|---|---|
| CN | 1312712 A | 9/2001 |
| EP | 267155 A2 | 5/1988 |
| JP | 5-070348 A | 3/1993 |
| WO | WO 80/02098 A1 | 10/1980 |
| WO | 98/08503 A1 | 3/1998 |
| WO | WO98/08503 * | 3/1998 |
| WO | WO 98/17662 A1 | 4/1998 |
| WO | WO 99/49862 A1 | 10/1999 |

(Continued)

OTHER PUBLICATIONS

Khoshyomn, et al, Synergistic Action of Genistein and Cisplatin on Growth Inhibition and Cytotoxicity of Human Medulloblastoma Cells,Pediatric Neurosurgery; Sep. 2000; 33, 3; p. 123-131.*

(Continued)

*Primary Examiner* — Gollamudi S Kishore
*Assistant Examiner* — Benjamin Packard
(74) *Attorney, Agent, or Firm* — Sughrue Mion, PLLC

(57) ABSTRACT

This invention relates to combination therapies involving anticancer chemotherapeutic agents and isoflavones or analogues thereof. The invention further relates to compounds, methods and therapeutic uses involving, containing, comprising, including and/or for preparing platinum-isoflavonoid complexes suitable for use in the combination therapies of the invention.

7 Claims, 8 Drawing Sheets

FOREIGN PATENT DOCUMENTS

| WO | 00/03707 A1 | 1/2000 |
|---|---|---|
| WO | WO 00/66576 A1 | 11/2000 |
| WO | 01/17986 A1 | 3/2001 |
| WO | WO 02/02548 A1 | 1/2002 |
| WO | 03/086386 A1 | 10/2003 |

OTHER PUBLICATIONS

Suggitt and Bibby, Clinical Cancer Research, 2005, vol. 11, 971-981.*

STN File Medline, abstract accession No. 2003459262 & Tamura S. et al., Pigment Cell Research, (Oct. 2003) 16 (5) 470-6, "Genistein enhances the ciplatin-induced inhibitions of cell growth and apoptosis in human malignant melanoma cells".

STN File Biosis, abstract accession No. 2003:368481 & Mansour A. et al., Blood (Nov. 16, 2002) vol. 100, No. 11, pp. Abstract No. 4997, "Enhancement of chemotherapeutic efficacy by combining agents that block IL-10 in CIL cell lines".

STN File Medline, abstract accession No. 2002151803 & S. Giacomelli et al., Life Sciences (Feb. 8, 2002), pp. 1447-1459, "Silybin and its bioavailable phospholipids complex (IdB 1016) potentiate in vitro and in vivo in the activity of cisplatin".

STN File Medline, abstract accession No. 2000404390 & Caltagirone S. et al, International Journal of Cancer (Aug. 15, 2000), 87 (4), pp. 595-600, "Flavanoids apigenin and quercetin inhibit melanoma growth and metastatic potential".

STN File Medline, abstract accession No. 96273517 & Scambia G. et al, European Journal of Cancer (May 1996), 32A(5), pp. 877-882, "Antiproliferative effect of silybin on gynaecological malignancies: synergism with cisplatin and doxorubicin".

STN File Medline, abstract accession No. 91191699 & Waud W. R. et al, Cancer Chemotherapy and Pharmacology (1991), 27(6), pp. 456-463, "Antitumor drug cross-resistance in vivo in a cisplatin-resistant murine P388 leukemia".

STN File Medline, abstract accession No. 91107211 & Neelam S. S. et al, Investigational New Drugs (Aug. 1990), 8 (3), pp. 263-268, "Combination of flavone acetic acid (FAA) with adriamycin, cisplatinum and difluoromethylornithine (DFMO) in vitro against human colon cancer cells".

STN File Medline, abstract accession No. 92032982 & Scambia G. et al, Anti-Cancer Drugs (Oct. 1990), 1 (1), pp. 45-48, "Synergistic antiproliferative activity of quercetin and cisplatin on ovarian cancer cell growth".

STN File CA, abstract No. 119:131038 & De Vincenzo R. et al, Acta Medica Romana (1992), 30 (1-2), pp. 126-132, "Flavanoids and negative control of cell proliferation in ovarian tumors".

Zyner E. et al, Acta Poloniae Pharmaceutica Drug Research, 1999, 56(2), pp. 159-167, "Platinum (II) and palladium (II) N, O-chelates with substituted flavanone containing ligands".

Zyner E. et al, Pharmazie, 1999, 54 (12), pp. 945-946, "Pt (II) and Pd (II) complexes of 3-aminoflavone: in vitro and in vivo evaluation".

Lei W. et al, Anticancer Research, 1999, vol. 19, pp. 221-228, "Enhancement of chemosensitivity and programmed cell death by tyrosine kinase inhibitors correlates with EGFR expression in non-small cell lung cancer cells".

Kang B-J et al, Natural Product Sciences, 2000, 6(4), pp. 165-169, "Scientific analysis of formulation theory of Chungpesagan-tang; in vitro cytotoxicity of cisplatin combined with Chungpesagan-tang".

Sepulveda-Boza, S et al, "The Preparation of New Isoflavones", Synthetic Communications (2001) vol. 31 No. 12 pp. 1933-1940.

O'Neil, M J. et al, "Inducible Isoflavonoids from the Lima Bean, Phaseolus lunatus", Phytochemistry (1986) vol. 25, No. 6 pp. 1315-1322.

Wolfbeis, O S et al, "The Absorption and Fluorescence of Isoflavones and the Effect of Shift Regents", Z. Naturforsch (1984) 39b pp. 238-243.

Arora, S K et al, "The Synthesis of Tlatlancuayin", Tetrahedron (1962) vol. 18 pp. 559-565.

STN Chemical Abstract Accession No. 135: 355315 & Chemical and Pharmaceutical Bulletin (2001), 49 (9), 1229-1231.

STN Chemical Abstract Accession No. 135:121648 & Journal of Agricultural and Food Chemistry (2001), 49 (6) 3024-3033.

STN Chemical Abstract Accession No. 124:341448 & Archives of Microbiology (1995), 164 (6), 428-34.

STN Chemical Abstract Accession No. 124:316797 & Chemical and Pharmaceutical Bulletin (1996), 44 (3), 486-91.

STN Chemical Abstract Accession No. 124: 140985 & Tennen Yuki Kagobutsu Toronkai Koen Yoshishu (1995), 37$^{th}$, 493-8.

STN Chemical Abstract Accession No. 115:68424 & Phytochemistry (1991), 30 (4), 1281-4.

STN Chemical Abstract Accession No. 114:41246 & Angewandte Botanik (1990), 64 (1-2), 175-90.

STN Chemical Abstract Accession No. 112:69573 & International Journal of Tissue Reactions (1989), 11 (3), 107-12.

STN Chemical Abstract Accession No. 102:59329 & Phytochemistry (Elsevier) (1984), 23 (11), 2703-4.

STN Chemical Abstract Accession No. 102:59220 & Phytochemistry (Elsevier) (1984), 23 (6), 1342-3).

STN Chemical Abstract Accession No. 97:109739 & J. Chem. Soc., Perkin Trans. 1 (1982), (6), 1389-94.

STN Chemical Abstract Accession No. 95:111690 & Phytochemistry (1981), 20 (4), 799-801.

STN Chemical Abstract Accession No. 82:97918 & J. Inst. Chem., Calcutta (1974), 46, Pt. 3, 61-5.

STN Chemical Abstract Accession No. 76:140428 & J. Inst. Chem., Calcutta (1971), 43 (6), 234-40.

STN Chemical Abstrac Accession No. 70:57577 Indian J. Chem. (1968), 6 (9), 481-4.

STN Chemical Abstract Accession No. 63:54547 & Bull. Chem. Soc. Japan (1965), 38 (6), 887-93.

STN Chemical Abstract Accession No. 61:61569 & Periodica Polytech. (1963), 7 (4), 241-58.

STN Chemical Abstract Accession No. 126:139728 (see CAS RN 116718-84-4) & Atherosclerosis (1997), 128 (1), 59-66.

Jha, H C et al, "Carbon-13 Chemical Shift Assignments of Chromones and Isoflavones", Can. J. Chem. (1980) vol. 58 No. 12 pp. 1211-1219.

STN Chemical Abstracts Accession No. 128:164027 & Antioxidants in Health and Disease (1998), 7 (Flavanoids in Health and Disease) pp. 295-302.

STN Chemical Abstracts Accession No. 117:124019 & Biochemical Pharmacology (1992) vol. 44 (1), pp. 157-162.

Abstract XP002541865, "Phenoxodiol enters phase II leukemia trial", DailyDrugNews.com (Daily Essentials), Sep. 26, 2002.

Andreas I. Constantinou, et al., "Phenoxodiol (2H-1-Benzopyran-7-0,1,3-(4-hydroxyphenyl)), A Novel Isoflavone Derivative, Inhibits DNA Topoisomerase II by Stabilizing the Cleavable Complex", Anticancer Research, vol. 22, No. 5, pp. 2581-2586, Sep. 2002.

Tito Fojo, et al., "Taxol and other microtubule-interactive agents", Current Opinion in Oncologic, Endocrine and Metabolic Investigational Drugs, vol. 2, No. 3, pp. 293-304, Jan. 1, 2000.

Dirk Th. Sleijfer, et al., "Cisplatin: a review of clinical applications and renal toxicity", Pharmaceutish Weekblad Scientific Edition, vol. 7, No. 6, pp. 237-244, Dec. 13, 1985.

Antona J. Wagstaff, et al., "Carboplatin. A preliminary review of its pharmacodynamic and pharmacokinetic properties and therapeutic efficacy in the treatment of cancer", Drugs, vol. 37, No. 2, pp. 162-190, Feb. 1989.

Supplemental European Search Report dated Sep. 4, 2009, issued in European Application No. 03798829.2.

H. Adlercreutz, et al., "Determination of Urinary Lignans and Phytoestrogen Metabolites, Potential Antiestrogens and Anticarcinogens, In Urine of Women on Various Habitual Diets", Proceedings of the XII International Study Group for Steroid Hormones, (Rome, Dec. 2-4, 1985), pp. 791-797.

Beverly A. Teicher, et al., "Comparison of several antiangiogenic regimens alone and with cytotoxic therapies in the Lewis lung carcinoma", Cancer Chemother Pharmacol (1996) 38: 169-177.

Sara Caltagirone, et al., "Flavonoids Apigenin and Quercetin Inhibit Melanoma Growth and Metastatic Potential", Int. J. Cancer: 87, (2000), pp. 595-600.

Hilary J. Cross, et al., "Effect of Quercetin on the Genotoxic Potential of Cisplatin", Int. J. Cancer: 66 (1996), pp. 404-408.

Johann Hofmann, et al., "Enhancement of the Antiproliferative Activity of Cis-Diamminedichloroplatinum(II) by Quercetin", Int. J. Cancer: 45, (1990), pp. 536-539.

Morag C.E. McFadyen, et al., "Cytochrome P450 CYP1B1 protein expression: a novel mechanism of anitcancer drug resistance", Biochemical Pharmacology 62 (2001), pp. 207-212.

Yasuyuki Sadzuka, et al., "Efficacies of tea components on doxorubicin induced antitumor activity and reversal of multidrug resistance", Toxicology Letter 114, (2000) pp. 155-162.

Agnieszka Siwinska, et al., "Potentiation of the Antiproliferative Effect in Vitro of Doxorubicin, Cisplatin and Genistein by New Analogues of Vitamin D", Anticancer Research 21: (2001), pp. 1925-1930.

Justyna Stawinska, et al., "The reactivity of cis-platin. Spectroscopic properties of products isolated from the [cis-Pt($NH_3$)$_2$$CI_2$-quercetin] and [cis-Pt($NH_3$)$_2$$CI_2$-$Cr^{VI}$-quercetin] systems," Transition Metal Chemistry 26: 2001, pp. 153-159.

Yuichiro Takeda, et al, "Reversal of Multidrug Resistance by Tyrosine-Kinase Inhibitors in a Non-P-Glycoprotein-Mediated Multidrug-Resistant Cell Line", Int. J. Cancer: 57, (1994), pp. 229-239.

Elzbieta Zyner, et al,"Platinum(II) and Palladiurn(II) N,O-Chelates With Substituted Flavanone Containing Ligands", Drug Research, vol. 56, No. 2, 1999, pp. 159-167.

Database Medline—XP008099672 & Am J Resp Cell 1997, 17, 51-59.

Cronauer, M. et al., "Inhibitory Effects of the Nucleoside Analogue Gemcitabine on Prostatic Carcinoma Cells", The Prostate, 28:172-181 (1996).

Neale, M. et al., "The ex vivo effect of high concentrations of doxorubicin on recurrent ovarian carcinoma", Anti-Cancer Drugs 2000, vol. 11, pp. 865-871.

* cited by examiner

COMBINATION CHEMOTHERAPY COMPOSITIONS AND METHODS

This application is a 371 of PCT/AU2003/001296, filed Oct. 2, 2003; the disclosure of which is incorporated herein by reference.

FIELD OF THE INVENTION

This invention relates to combination therapies involving anticancer chemotherapeutic agents and isoflavones or analogues thereof. The invention further relates to compounds, compositions, methods and therapeutic uses involving, containing, comprising, including and/or for preparing platinum-isoflavonoid complexes suitable for use in the combination therapies of the invention.

BACKGROUND

The regulation of cell division (mitosis) is of critical importance to the normal growth and development of a multicellular organism, as well as the homeostatic maintenance of tissues, and the ability of certain cell types to respond appropriately to environmental cues.

Loss of control of normal cell proliferation rate occurs when the "checkpoints" of cell division fail to function normally. This occurs when normal cells acquire basic genetic damage through somatic mutations to key regulatory genes or through genetic inheritance, thus becoming "initiated" cells. The genetic abnormalities in initiated cells lead to altered gene expression and altered cell behaviour.

The initiated cells may undergo clonal expansion and act as a site for additional genetic alteration. Cell proliferation acts to push clonal expansion. Should further genetic damage occur, the initiated cells can eventually accumulate sufficient genetic damage to cell-cycle regulatory genes to form neoplastic cells, resulting in a neoplastic cell mass or neoplasm.

Neoplasms are generally classified as benign or malignant. Benign tumours proliferate locally and are composed of differentiated cells resembling those of the tissue of origin, the edge of the tumour remaining well defined, and usually encapsulated. Malignant neoplasms (classically termed "cancers") are not encapsulated and their edges are ill-defined, the cells are also less well differentiated than the cells of origin, and show increased mitotic activity.

Localised, chronic irritation or inflammation can also cause cells to divide abnormally, resulting in abnormal growths or cellular masses, or tumours. Reactive cellular growth responses to clearly defined, chronic irritant stimulation are described as metaplasias. In dysplasias, there is a disorganisation of the pattern of squamous epithelium in tissues such as the skin, oesophagus and uterus in response to chronic irritation or inflammation.

Numerous compounds are commercially available as chemotherapeutic agents for destruction of abnormally proliferating cells in benign and malignant neoplasias, dyplasias and metaplasias. Predicting the responsiveness of a given tumour-related disease type to a particular drug is difficult, as each disease type is different and may respond to different treatments. Generally, clinical treatment of cancer and other cellular proliferative disorders involves having different chemotherapy treatment options for each condition.

An example of an important chemotherapeutic agent is the platinum-based compound cisplatin (cis-diamminedichloroplatinum (II); cis-$Cl_2(NH_3)$Pt). Cisplatin has a square planar geometry, with each of the two chloride groups (and likewise, each of the two amine groups) being adjacent, or cis, to each other.

Cisplatin was first approved for human use in the late 1970's and is prescribed for the treatment of a variety of tumours including germ-cell, advanced bladder carcinoma, adrenal cortex carcinoma, breast, testicular and ovarian cancer, head and neck carcinoma and lung carcinoma.

Cisplatin is active against proliferating or cancerous cells by binding to DNA and interfering with its repair mechanism, eventually leading to cell death. It is thought that the first step in the cellular process is that a molecule of water replaces one of the chloride ions of cisplatin. The resulting intermediate structure can then bind to a single nitrogen on a DNA nucleotide. Following that, the second chloride is also replaced by another water molecule and the platinum agent then binds to a second nucleotide. Binding studies of cisplatin with DNA have indicated a preference for nitrogen 7 on two adjacent guanines on the same strand. It also binds to adenine and across strands to a lesser extent.

The binding of cisplatin to DNA causes production of intrastrand cross-links and formation of DNA adducts. The adducts or cisplatin-DNA complexes attract the attention of DNA repair proteins which become irreversibly bound. The resulting distortion to the shape of the DNA by the binding of cisplatin prevents effective repair and hence, cell death.

Other well known chemotherapeutic agents include carboplatin, the taxanes such as paclitaxel, gemcitabine, 5-fluorouracil, methotrexate and the tetracyclines.

Patients undergoing cancer chemotherapy often have to contend with quite severe and debilitating side effects due to the toxicity of the active agents. Common side effects of chemotherapy are nausea and vomiting. Other side effects include temporary reduction in bone marrow function, numbness or tingling in hands or feet, changes in hearing, temporary taste alterations, loss of appetite, diarrhoea and allergic reactions.

Chemotherapy regimes are further complicated by the efficacy of currently available chemotherapeutic agents against various cancers or other tumour types sometimes being insufficient. For example, some cancer cells have developed natural tolerance against the therapeutic agents. Further, some therapeutic or prophylactic agents exert side effects, or can induce the development of tolerance in abnormally dividing cells during clinical use, leading to a situation in which certain tumour types become multiply drug resistant. Multidrug resistance thus remains a main complication of long-term successful tumour chemotherapy.

Accordingly there is a strong need to identify new, improved, better and/or alternative pharmaceutical compositions, agents and treatment regimes against chemosensitivity, mutated growth or proliferation of cells including cancer and related diseases. There is a further need for chemotherapeutic agents which address some of the undesirable side effects of known agents. There is also a need for different therapies to be available to physicians to combat the numerous and various types of cancers and to provide new options for treatment to address issues of tolerance of proliferating cells to the existing chemotherapeutic agents and treatment regimes. Agents which can act synergistically with other chemotherapeutics are highly sought after. Any beneficial effects which can be obtained with synergistic agents can reduce the amount and duration of traditional chemotherapeutic drugs or improve or restore chemoselectivity thereby providing safer administration and hopefully fewer or less sever side effects.

It is a preferred object of the present invention to provide pharmaceutical compositions and methods for the treatment, amelioration or prophylaxis of cancer and diseases associated with oxidant stress. The present invention also seeks to provide pharmaceutical compositions and methods for targeting neoplastic cells for treatment, which compositions and methods provide improved cell activity in terms of targeting function, improved delivery of toxic agents and/or improvement or restoration of chemosensitivity.

SUMMARY OF THE INVENTION

This application now describes new treatment regimes and chemotherapeutic compositions and compounds. The invention is based on the totally unexpected activity of isoflavonoid compounds in restoring or addressing the chemoselectivity or activity of anticancer agents, synergistic compositions including same and novel isoflavonoid-drug complexes.

According to an aspect of the present invention there is provided a method of increasing the sensitivity of cancer cells or a tumour to a chemotherapeutic agent by contacting said cells or tumour with an isoflavonoid compound of formula (I) as set out below.

Compounds of the general formula (I) are the isoflavonoid compounds represented by the formula:

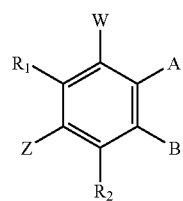

(I)

in which
$R_1$, $R_2$ and Z are independently hydrogen, hydroxy, $OR_9$, $OC(O)R_{10}$, $OS(O)R_{10}$, CHO, $C(O)R_{10}$, COOH, $CO_2R_{10}$, $CONR_3R_4$, alkyl, haloalkyl, arylalkyl, alkenyl, alkynyl, aryl, heteroaryl, alkylaryl, alkoxyaryl, thio, alkylthio, amino, alkylamino, dialkylamino, nitro or halo, or
$R_2$ is as previously defined, and $R_1$ and Z taken together with the carbon atoms to which they are attached form a five-membered ring selected from

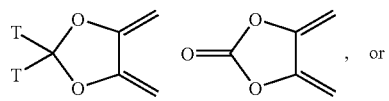, or $R_1$ is as previously defined, and $R_2$ and Z taken together with the carbon atoms to which they are attached form a five-membered ring selected from

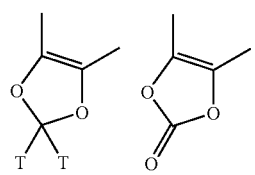

and
W is $R_1$, A is hydrogen, hydroxy, $NR_3R_4$ or thio, and B is selected from

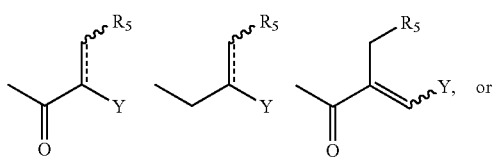

W is $R_1$, and A and B taken together with the carbon atoms to which they are attached form a six-membered ring selected from

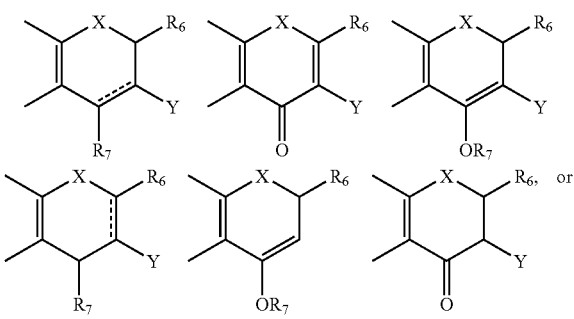

W, A and B taken together with the groups to which they are associated are selected from

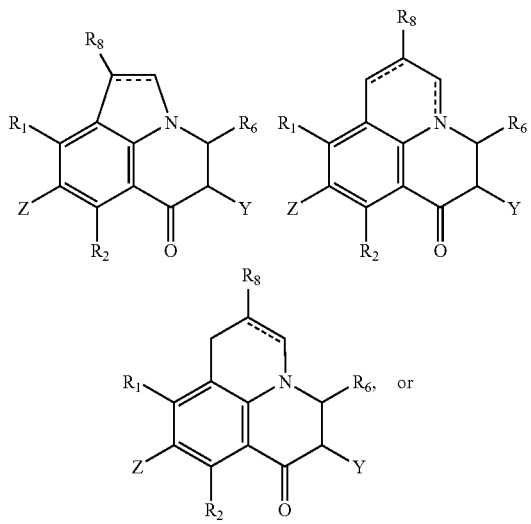

W and A taken together with the groups to which they are associated are selected from

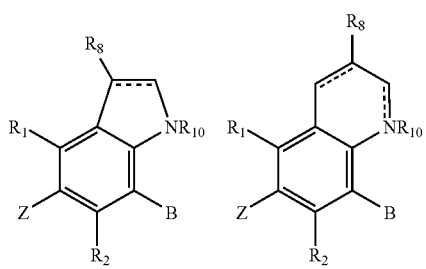

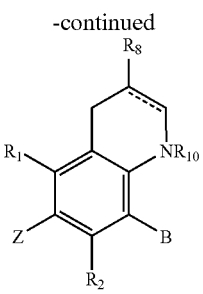

and B is selected from

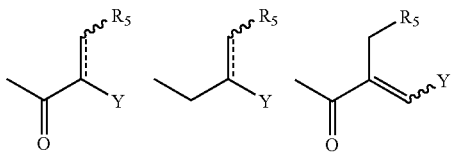

wherein
$R_3$ is hydrogen, alkyl, arylalkyl, alkenyl, aryl, an amino acid, $C(O)R_{11}$ where $R_{11}$ is hydrogen, alkyl, aryl, arylalkyl or an amino acid, or $CO_2R_{12}$ where $R_{12}$ is hydrogen, alkyl, haloalkyl, aryl or arylalkyl,
$R_4$ is hydrogen, alkyl or aryl, or
$R_3$ and $R_4$ taken together with the nitrogen to which they are attached comprise pyrrolidinyl or piperidinyl,
$R_5$ is hydrogen, $C(O)R_{11}$ where $R_{11}$ is as previously defined, or $CO_2R_{12}$ where $R_2$ is as previously defined,
$R_6$ is hydrogen, hydroxy, alkyl, aryl, amino, thio, $NR_3R_4$, $COR_{11}$ where $R_{11}$ is as previously defined, $CO_2R_{12}$ where $R_{12}$ is as previously defined or $CONR_3R_4$,
$R_7$ is hydrogen, $C(O)R_{11}$ where $R_{11}$ is as previously defined, alkyl, haloalkyl, alkenyl, aryl, arylalkyl or $Si(R_{13})_3$ where each $R_{13}$ is independently hydrogen, alkyl or aryl,
$R_8$ is hydrogen, hydroxy, alkoxy or alkyl,
$R_9$ is alkyl, haloalkyl, aryl, arylalkyl, $C(O)R_{11}$ where $R_{11}$ is as previously defined, or $Si(R_{13})_3$ where $R_{13}$ is as previously defined,
$R_{10}$ is hydrogen, alkyl, haloalkyl, amino, aryl, arylalkyl, an amino acid, alkylamino or dialkylamino, the drawing "- - - -" represents either a single bond or a double bond,
T is independently hydrogen, alkyl or aryl,
X is O, $NR_4$ or S, and
Y is

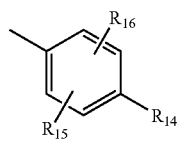

wherein
$R_{14}$, $R_{15}$ and $R_{16}$ are independently hydrogen, hydroxy, $OR_9$, $OC(O)R_{10}$, $OS(O)R_{10}$, CHO, $C(O)R_{10}$, COOH, $CO_2R_{10}$, $CONR_3R_4$, alkyl, haloalkyl, arylalkyl, alkenyl, alkynyl, aryl, heteroaryl, thio, alkylthio, amino, alkylamino, dialkylamino, nitro or halo, or any two of $R_{14}$, $R_{15}$ and $R_{16}$ are fused together to form a cyclic alkyl, aromatic or heteroaromatic structure, and pharmaceutically acceptable salts thereof.

In a preferred embodiment the cancer cells or tumour are pre-treated with a compound of formula (I), prior to treatment with the chemotherapeutic agent.

In another embodiment, the compound of formula (I) is administered concurrently with the chemotherapeutic agent.

In a further embodiment the compound of formula (I) is administered after resistance to a chemotherapeutic agent is observed in cancer cells and tumours, and in particular after multidrug resistance is observed.

In a further embodiment the sensitivity of the cancer cells or tumour to the chemotherapeutic agent is restored or regenerated.

According to another aspect there is provided a combination therapy comprising administering to a subject a therapeutically effective amount of a compound of formula (I) and a chemotherapeutic agent.

The combination therapy is for the treatment, prophylaxis, amelioration, defence against and/or prevention of cell proliferation and cancers including benign prostatic hypertrophy; breast cancer; uterine cancer; ovarian cancer; testicular cancer; large bowel cancer; endometrial cancer; prostatic cancer; uterine cancer; and diseases associated with oxidant stress including cancer, myocardial infarction stroke, arthritis, sunlight induced skin damage or cataracts (for convenience hereafter referred to as the "therapeutic indications").

In a preferred embodiment the administration of the compound of formula (I) precedes the administration of the chemotherapeutic agent. Alternatively, the administration is concurrent. In a further embodiment the combination therapy follows observed resistance by cancer cells and tumours to a chemotherapeutic agent or agents.

In a preferred embodiment the subject cell growth is proliferation, and the subject down-regulation is killing off the proliferating cells. The condition being treated is preferably cancer, more preferably a metastatic cancer selected from breast cancer, prostatic cancer, testicular cancer, ovarian cancer, uterine cancer and/or colorectal cancer, and more preferably is ovarian cancer, prostatic cancer or pancreatic cancer.

In further aspects of the invention there is provided methods for the manufacture of medicaments for the above stated methods of the invention and pharmaceutical agents useful for same.

This application also describes new therapeutic compositions and complexes comprising platinum-based pharmaceutical agents. The invention is based on the totally unexpected biological activity of new platinum-isoflavonoid complexes and of isoflavonoid compounds of formula (I) which form synergistic compositions or complexes with platinum-based chemotherapeutic agents.

The compositions and platinum-isoflavonoid complexes are important targeting agents for the delivery of toxic signals to cells. The compositions and methods of the invention are directed to treating a condition in a subject, which condition is characterised by the undesirable, detrimental or otherwise unwanted growth or proliferation of cells.

According to an aspect of this invention there is provided platinum-isoflavonoid complexes and analogues thereof described by general formula (II):

in which $R_A$, $R_B$, $R_C$, and $R_D$ are independently halo, hydroxy, $XR_E$, alkoxy, $OC(O)R_F$, $OS(O)R_F$, thio, alkylthio, amino, alkylamino or dialkylamino, X is O, $NR_F$ or S, and $R_F$ is hydrogen, alkyl, arylalkyl, alkenyl, aryl or an amino acid, wherein at least one of $R_A$, $R_B$, $R_C$, and $R_D$, and preferably only $R_A$, is $XR_E$ where $R_E$ is an isoflavonoid compound represented by general formula (I) set out above or is derived from or is a radical or ion of the isoflavonoid compound (I) and ligates to the platinum through any one or more of the heteroatoms X or a radical of the heteroatoms defined as part of $R_E$ or alternatively by a double bond on the isoflavonoid compound (I) and when $R_A$ is $XR_E$, $R_B$, $R_C$ and/or $R_D$ together may form part of a bidentate or tridentate ligand of general formulae (B) and (T) respectively

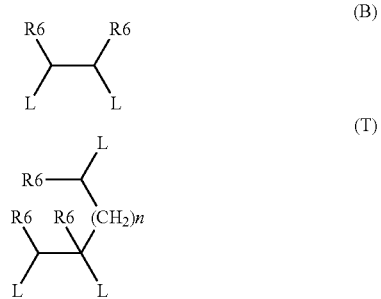

wherein L represents a ligating atom chosen from N, O and S, n is from 0 to 8, and each $R_6$ is independently as defined above or may together form part of a cyclic alkyl, aromatic or heteroaromatic structure, which platinum-isoflavonoid complexes include pharmaceutically acceptable salts thereof.

It has also surprisingly been found by the inventors that platinum-isoflavonoid complexes of the general formula (II) have particular utility and effectiveness in the treatment, prophylaxis, amelioration defence against, and/or prevention of the therapeutic indications noted above.

Thus according to another aspect of the present invention there is provided a method for the treatment, prophylaxis, amelioration, defence against, and/or prevention of the therapeutic indications described above which method comprises administering to a subject a therapeutically effective amount of one or more platinum-isoflavonoid complexes of the formula (II) as defined above.

Another aspect of the present invention provides a method of treating a condition in a mammal, which condition is characterised by the undesirable, detrimental or otherwise unwanted growth of cells, said method comprising administering to said mammal an effective amount a platinum-isoflavonoid complex of formula (II) for a time and under conditions sufficient to down-regulate the growth of said cells.

In a preferred embodiment the subject cell growth is proliferation, and the subject down-regulation is killing off the proliferating cells. The condition being treated is preferably cancer, more preferably a metastatic cancer selected from breast cancer, prostatic cancer, testicular cancer, ovarian cancer, uterine cancer and/or colorectal cancer, and more preferably is ovarian cancer, prostatic cancer or pancreatic cancer.

Another aspect of the present invention provides a method of down-regulating the growth of cells, said method comprising contacting said cells with an effective amount of a platinum-isoflavonoid complex of formula (II).

In a preferred embodiment the subject cell growth is proliferation, and the subject down-regulation is killing off the proliferating cells.

Another aspect of the present invention provides the use of platinum-isoflavonoid complexes of the formula (II) for the manufacture of a medicament for the treatment, amelioration, defence against, prophylaxis and/or prevention of one or more of the therapeutic indications.

Another aspect of the present invention provides the use of one or more platinum-isoflavonoid complexes of the formula (II) in the treatment, amelioration, defence against, prophylaxis and/or prevention of one or more of the therapeutic indications.

Another aspect of the present invention provides an agent for the treatment, prophylaxis, amelioration, defence against and/or treatment of the therapeutic indications which comprises one or more platinum-isoflavonoid complexes of the formula (II) either alone or in association with one or more carriers or excipients.

Another aspect of the invention provides a therapeutic composition which comprises one or more platinum-isoflavonoid complexes of the formula (II) in association with one or more pharmaceutical carriers and/or excipients.

Another aspect of the present invention provides a drink or food-stuff, which contains one or more platinum-isoflavonoid complexes of the formula (II).

The present invention also provides compositions comprising a platinum complex of the general formula (IIa),

in which $R_G$, $R_H$, $R_I$, and $R_J$ are independently halo, hydroxy, alkoxy, $OC(O)R_K$, $OS(O)R_K$, thio, alkylthio, amino, alkylamino or dialkylamino, X is O, $NR_K$ or S, and $R_K$ is hydrogen, alkyl, arylalkyl, alkenyl, aryl or an amino acid, or a pharmaceutically acceptable salt thereof, and an isoflavonoid compound of general formula (I) as defined above.

These compositions comprising a platinum complex of the formula (IIa) and an isoflavonoid compound of the formula (I) are found to have particular utility, effectiveness and synergism in the treatment, prophylaxis, amelioration defence against, and/or prevention of the therapeutic indications set out above.

Thus according to another aspect of the present invention there is provided a method for the treatment, prophylaxis, amelioration, defence against, and/or prevention of the therapeutic indications which comprises administering to a subject a therapeutically effective amount of compositions comprising a platinum complex of the formula (IIa) in conjunction with an isoflavonoid compound of formula (I).

Another aspect of the present invention provides the combined use of a platinum complex of the formula (IIa) and an isoflavonoid compound of the formula (I) in the manufacture of a medicament for the treatment, amelioration, defence against, prophylaxis and/or prevention of the therapeutic indications.

Another aspect of the present invention provides the use of a platinum complex of the formula (IIa) and an isoflavonoid compound of the formula (I) in the treatment, amelioration, defence against, prophylaxis and/or prevention of the therapeutic indications.

Another aspect of the present invention provides a kit comprising a platinum complex of the formula (IIa) and an isoflavonoid compound of the formula (I) either alone or in association with one or more carriers or excipients.

Another aspect of the present invention provides an agent for the treatment, prophylaxis, amelioration, defence against and/or treatment of the therapeutic indications which comprises a composition comprising a platinum complex of the formula (IIa) and an isoflavonoid compound of the formula (I) either alone or in association with one or more carriers or excipients.

Throughout this specification and the claims which follow, unless the text requires otherwise, the word "comprise", and variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

Figure 1:
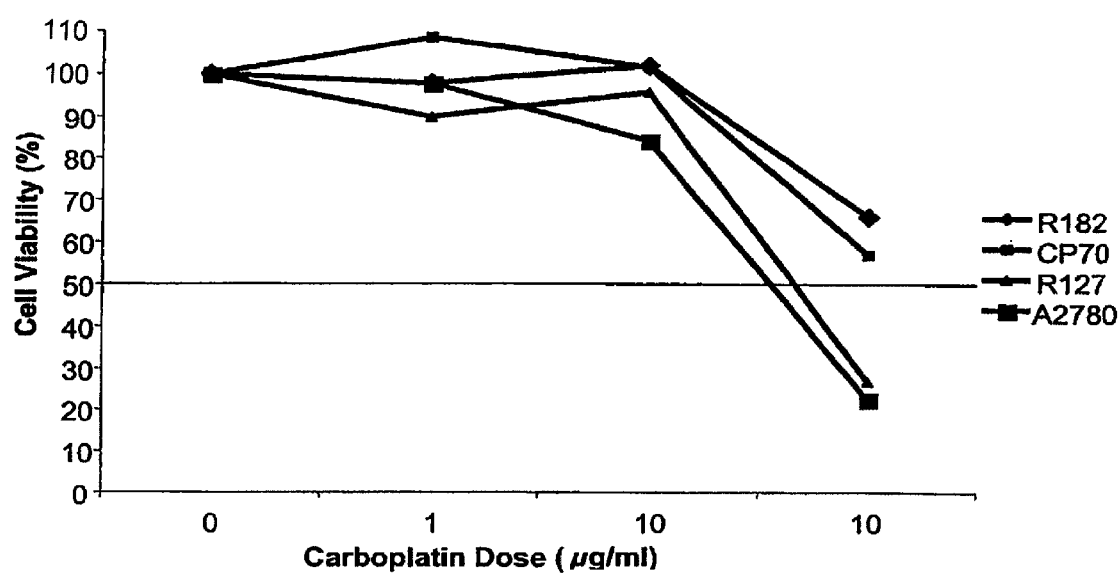
FIG. 1 represents the cell viability of various cancer cell lines over different concentrations of carboplatin.

The terms "isoflavonoid", "isoflavonoid" and "isoflavone" as used herein are to be taken broadly to include ring-fused benzopyran molecules having a pendent phenyl group from the pyran ring based on a 1,2-diphenylpropane system. Thus, the classes of compounds generally referred to as isoflavones, isoflavenes, isoflavans, isoflavanones, isoflavanols and the like are generically referred to herein as isoflavones, isoflavone derivatives or isoflavonoid compounds.

The term "alkyl" is taken to mean both straight chain and branched chain alkyl groups such as methyl, ethyl, propyl, isopropyl, butyl, isobutyl, secbutyl, tertiary butyl, and the like. The alkyl group has 1 to 10 carbon atoms, preferably from 1 to 6 carbon atoms, more preferably methyl, ethyl propyl or isopropyl. The alkyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "aryl" is taken to include phenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy or halo.

The term "halo" is taken to include fluoro, chloro, bromo and iodo, preferably fluoro and chloro, more preferably fluoro. Reference to for example "haloalkyl" will include monohalogenated, dihalogenated and up to perhalogenated alkyl groups. Preferred haloalkyl groups are trifluoromethyl and pentafluoroethyl.

The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, citrate, bicarbonate and carbonate.

The term "pharmaceutically acceptable derivative" or "prodrug" refers to a derivative of the active compound that upon administration to the recipient, is capable of providing directly or indirectly, the parent compound or metabolite, or that exhibits activity itself. Prodrugs are included within the scope of the present invention.

As used herein, the terms "treatment", "prophylaxis" or "prevention", "amelioration" and the like are to be considered in their broadest context. In particular, the term "treatment" does not necessarily imply that an animal is treated until total recovery. Accordingly, "treatment" includes amelioration of the symptoms or severity of a particular condition or preventing or otherwise reducing the risk of developing a particular condition.

Preferred isoflavonoid compounds of formula (I) are selected from general formulae (III)-(IX), and more preferably are selected from general formulae (IV)-(IX):

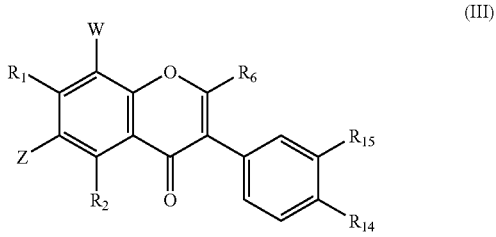

(III)

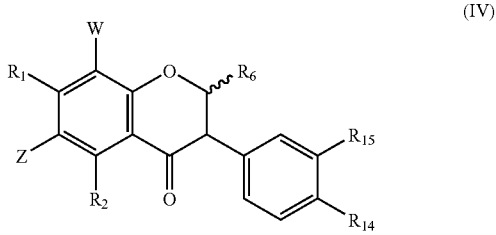

(IV)

-continued

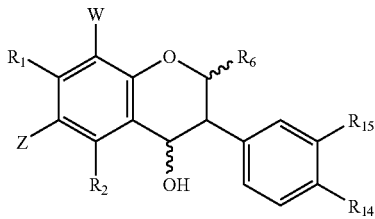
(V)

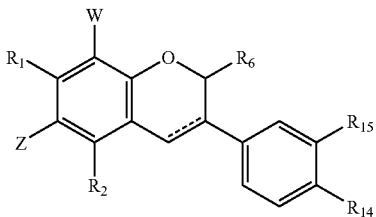
(VI)

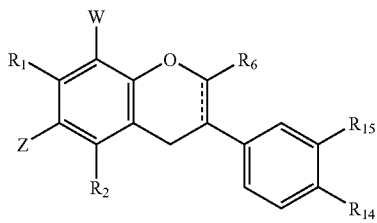
(VII)

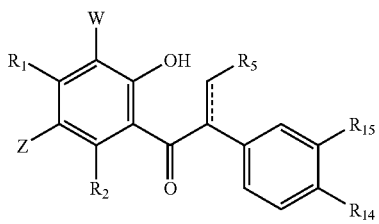
(VIII)

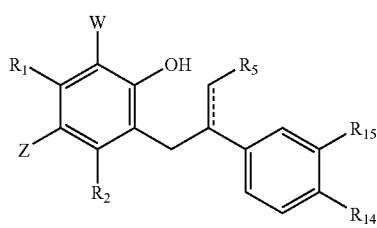
(IX)

in which
$R_1$, $R_2$, $R_5$, $R_6$, $R_{14}$, $R_{15}$, W and Z are as defined above,
more preferably
$R_1$, $R_2$, $R_{14}$, $R_{15}$, W and Z are independently hydrogen, hydroxy, $OR_9$, $OC(O)R_{10}$, $C(O)R_{10}$, COOH, $CO_2R_{10}$, alkyl, haloalkyl, arylalkyl, aryl, thio, alkylthio, amino, alkylamino, dialkylamino, nitro or halo,
$R_5$ is hydrogen, $C(O)R_{11}$ where $R_{11}$ is hydrogen, alkyl, aryl, or an amino acid, or $CO_2R_{12}$ where $R_{12}$ is hydrogen, alkyl or aryl,
$R_6$ is hydrogen, hydroxy, alkyl, aryl, $COR_{11}$ where $R_{11}$ is as previously defined, or $CO_2R_{12}$ where $R_{12}$ is as previously defined,
$R_9$ is alkyl, haloalkyl, arylalkyl, or $C(O)R_{11}$ where $R_{11}$ is as previously defined, and
$R_{10}$ is hydrogen, alkyl, amino, aryl, an amino acid, alkylamino or dialkylamino,
more preferably
$R_1$ and $R_{14}$ are independently hydroxy, $OR_9$, $OC(O)R_{10}$ or halo,
$R_2$, $R_{15}$, W and Z are independently hydrogen, hydroxy, $OR_9$, $OC(O)R_{10}$, $C(O)R_{10}$, COOH, $CO_2R_{10}$, alkyl, haloalkyl, or halo,
$R_5$ is hydrogen, $C(O)R_{11}$ where $R_1$, is hydrogen or alkyl, or $CO_2R_{12}$ where $R_{12}$ is hydrogen or alkyl,
$R_6$ is hydrogen or hydroxy,
$R_9$ is alkyl, arylalkyl or $C(O)R_{11}$ where $R_{11}$ is as previously defined, and
$R_{10}$ is hydrogen or alkyl,
and more preferably
$R_1$ and $R_{14}$ are independently hydroxy, methoxy, benzyloxy, acetyloxy or chloro,
$R_2$, $R_{15}$, W and Z are independently hydrogen, hydroxy, methoxy, benzyloxy, acetyloxy, methyl, trifluoromethyl or chloro,
$R_5$ is hydrogen or $CO_2R_{12}$ where $R_{12}$ is hydrogen or methyl, and
$R_6$ is hydrogen.

Particularly preferred isoflavonoid compounds of formula (I) are selected from:

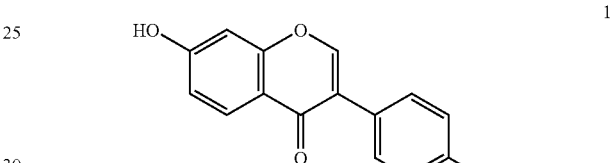
1

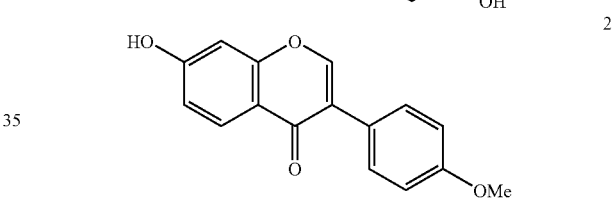
2

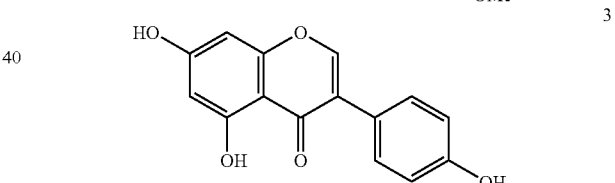
3

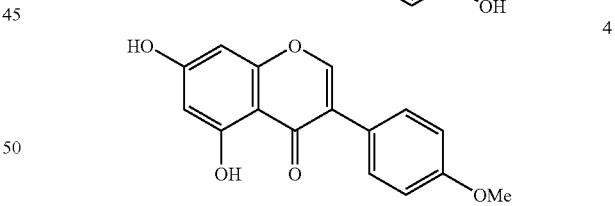
4

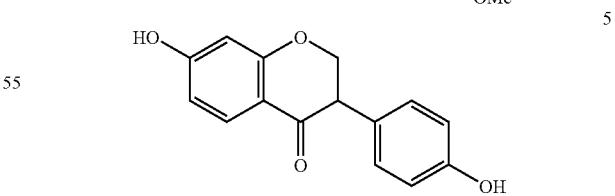
5

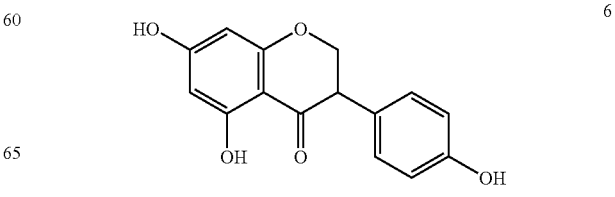
6

7
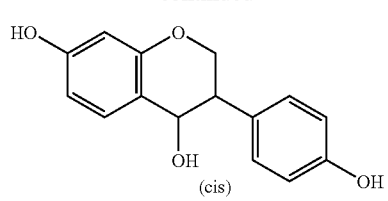
(cis)
8
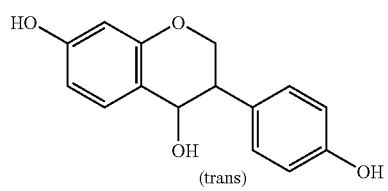
(trans)
9
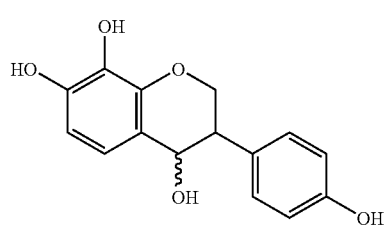
10
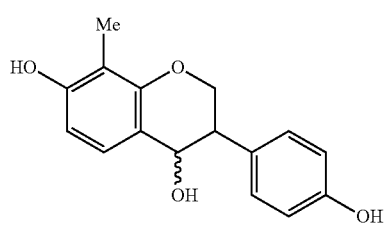
11
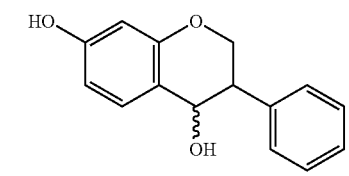
12
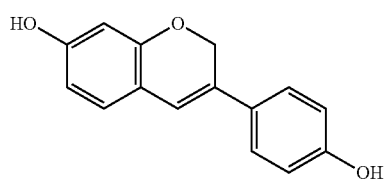
13
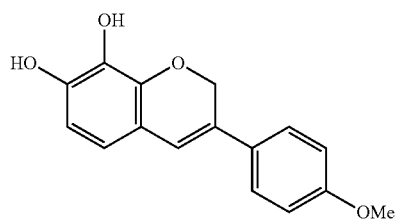
14
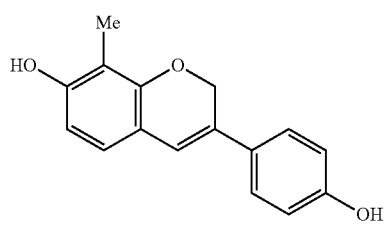
15
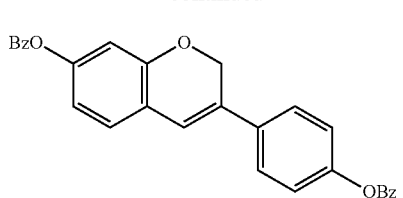
16
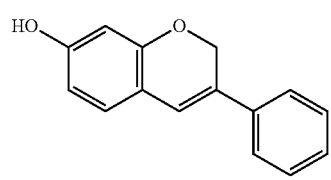
17
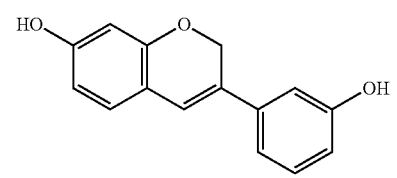
18
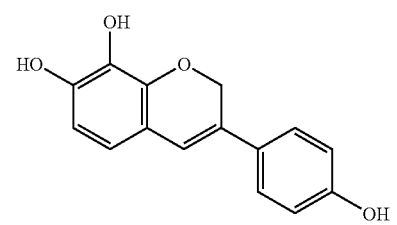
19
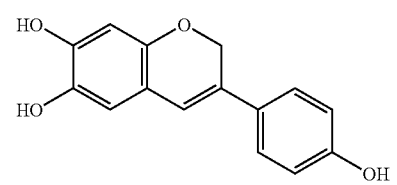
20
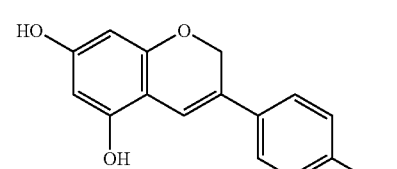
21
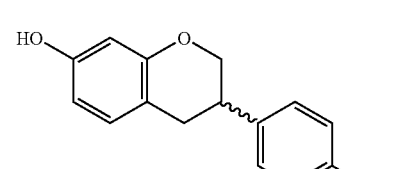
22
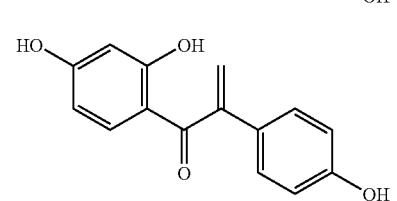

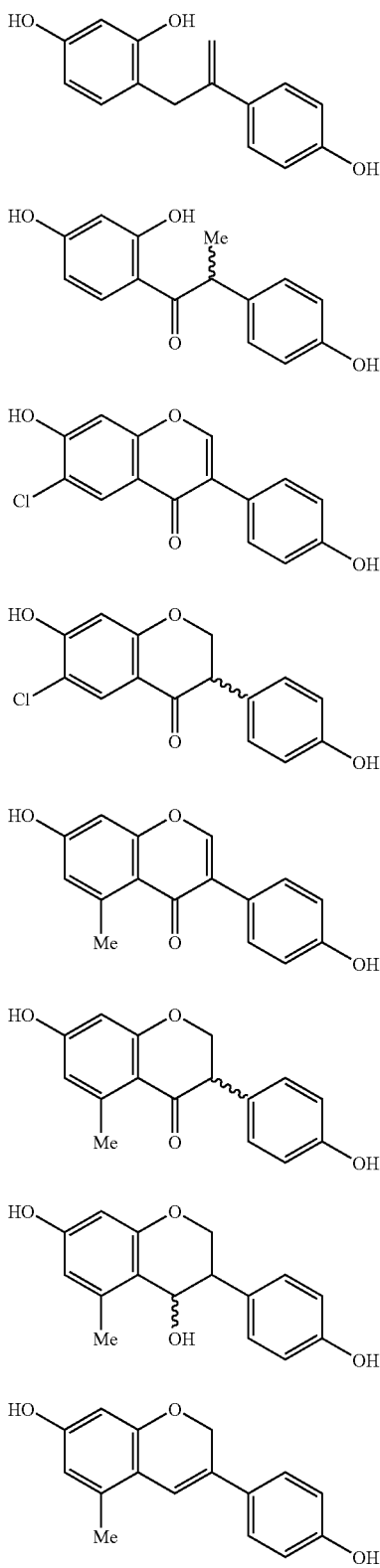

in which
R₁, R₂, R₆, R₁₄, R₁₅, W and Z are as defined above;
more preferably
$R_1$, $R_2$, $R_{14}$, $R_{15}$, W and Z are independently hydrogen, hydroxy, $OR_9$, $OC(O)R_{10}$, $C(O)R_{10}$, COOH, $CO_2R_{10}$, alkyl, haloalkyl, arylalkyl, aryl, thio, alkylthio, amino, alkylamino, dialkylamino, nitro or halo,
$R_6$ is hydrogen, hydroxy, alkyl, aryl, $COR_{11}$ where $R_{11}$ is as previously defined, or $CO_2R_{12}$ where $R_{12}$ is as previously defined,
$R_9$ is alkyl, haloalkyl, arylalkyl, or $C(O)R_{11}$ where $R_{11}$ is as previously defined, and
$R_{10}$ is hydrogen, alkyl, amino, aryl, an amino acid, alkylamino or dialkylamino,
more preferably
$R_1$ is hydroxy, $OR_9$, $OC(O)R_{10}$ or halo,
$R_2$, $R_{14}$, $R_{15}$, W and Z are independently hydrogen, hydroxy, $OR_9$, $OC(O)R_{10}$, $C(O)R_{10}$, COOH, $CO_2R_{10}$, alkyl, haloalkyl, or halo,
$R_6$ is hydrogen,
$R_9$ is alkyl, arylalkyl or $C(O)R_{11}$ where $R_{11}$ is as previously defined, and
$R_{10}$ is hydrogen or alkyl,
and more preferably
$R_1$ is hydroxy, methoxy, benzyloxy, acetyloxy or chloro,
$R_2$, $R_{14}$, $R_{15}$, W and Z are independently hydrogen, hydroxy, methoxy, benzyloxy, acetyloxy, methyl, trifluoromethyl or chloro, and
$R_6$ is hydrogen,
including pharmaceutically acceptable salts and derivatives thereof.

In a most preferred embodiment of the invention the isoflavonoid compound is dehydroequol, Cpd. 12. As such, particular reference is made to dehydroequol in the description, Examples which follow and accompanying drawings however this is not to be taken as being unnecessarily limiting on the disclosure of the invention provided herein.

Chemotherapeutic agents are generally grouped as DNA-interactive agents, antimetabolites, tubulin-interactive agents, hormonal agents, other agents such as asparaginase or hydroxyurea. Each of the groups of chemotherapeutic agents can be further divided by type of activity or compound. Chemotherapeutic agents used in combination with the isoflavonoid compound of formula (I) of the present invention, or salts thereof of the present invention, may be selected from any of these groups but are not limited thereto. For a detailed discussion of the chemotherapeutic agents and their method of administration, see Dorr, et al, Cancer Chemotherapy Handbook, 2d edition, pages 15-34, Appleton and Lang (Connecticut, 1994) herein incorporated by reference.

DNA-interactive agents include alkylating agents, e.g. cis-platin, cyclophosphamide, altretamine; DNA strand-breakage agents, such as bleomycin; intercalating topoisomerase II inhibitors, e.g., dactinomycin and doxorubicin); noninterca- In a further embodiment the preferred isoflavonoid compounds are the isoflav-3-ene and isoflavan compounds of general formula (VI), and more preferred are the 3-ene compounds of the general formula (VIa):

lating topoisomerase II inhibitors such as, etoposide and teniposide; and the DNA minor groove binder plicamydin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustinek, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin; and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules. Tubulin interactive agents include vincristine and vinblastine, both alkaloids and paclitaxel (Taxol), for example.

Hormonal agents are also useful in the treatment of cancers and tumors. They are used in hormonally susceptible tumors and are usually derived from natural sources. Hormonal agents include, but are not limited to, estrogens, conjugated estrogens and ethyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumour.

Preferred chemotherapeutic agents for use in the subject invention are cisplatin, carboplatin, taxol (paclitaxel), fluorouracil, fluxuridine, cyclophosphamide ifosfamide, hexamethylmelamine, estramustine, mitomycin, and docetaxel.

Compounds of formula (I) also exhibit chemotherapeutic activity and in this regard particular reference can be made to dehydroequol, Cpd. 12.

Preferred bidentate and tridentate platinum ligands of the present invention include those commonly known in the art. For example, suitable bidentate ligands may be selected from ethylene-1,2-diamine and 1,10-phenathraline and other ligands well known in the art.

Preferred platinum complexes are halo and amino substituted, more preferably chloro and amine substituted, more preferably cis-dichlorodiamino substituted. Preferred platinum-isoflavonoid complexes are preferably halo and amino substituted, more preferably cis-dichloroamino substituted or cis-diaminochloro substituted.

Compounds of the present invention have particular application in the treatment of diseases associated with or resulting from estrogenic effects, androgenic effects, vasolidatory and spasmodic effects, inflammatory effects and oxidative effects.

The amount of compounds of formulae (I), (II) or (I) and (IIa) which are required in a therapeutic treatment according to the invention will depend upon a number of factors, which include the specific application, the nature of the particular compound used, the condition being treated, the mode of administration and the condition of the patient. Compounds of formulae I or Ia and II may be administered in a manner and amount as is conventionally practised. See, for example, Goodman and Gilman, *The Pharmacological Basis of Therapeutics,* 1299 (7th Edition, 1985). The specific dosage utilised will depend upon the condition being treated, the state of the subject, the route of administration and other well known factors as indicated above. In general, a daily dose per patient may be in the range of 0.1 mg to 10 g; typically from 0.5 mg to 1 g; preferably from 50 mg to 200 mg. Importantly the synergistic relationship of the isoflavonoid compounds of general formula (I) and the chemotherapeutic agent allow for significant reductions in dosage regimes of relatively toxic drugs such as cisplatin, paclitaxel and carboplatin for example.

Other preferred dosage regimes and amounts are set out in the Examples and accompanying drawings.

The production of a pharmaceutical composition for the treatment of the therapeutic indications herein described (for convenience hereafter referred to as the "active compounds") are typically admixed with one or more pharmaceutically or veterinarially acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, optical, buccal (for example, sublingual), parenteral (for example, subcutaneous, intramuscular, intradermal, or intravenous) and transdermal administration, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound(s) and are administered at a rate of 0.1 ml/minute/kg or as appropriate. Parenteral administration is a preferred route of administration for the compounds of the present invention.

Formulations suitable for rectal administration are preferably presented as unit dose suppositories. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vaseline, lanoline, polyethylene glycols, alcohols, and combination of two or more thereof. The active compound is generally present at a concentration of from 0.1% to 0.5% w/w, for example, from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound.

Formulations suitable for transdermal administration may also be delivered by iontophoresis (see, for example, *Pharmaceutical Research* 3 (6), 318 (1986)) and typically take the form of an optionally buffered aqueous solution of the active compound. Suitable formulations comprise citrate or bis/tris buffer (pH 6) or ethanol/water and contain from 0.1 M to 0.2 M active ingredient.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Therapeutic methods, uses and compositions may be for administration to humans and other animals, including mammals such as companion and domestic animals (such as dogs and cats) and livestock animals (such as cattle, sheep, pigs and goats), birds (such as chickens, turkeys, ducks) and the like.

The active compound or pharmaceutically acceptable derivatives prodrugs or salts thereof can also be co-administered with other active materials that do not impair the desired action, or with materials that supplement the desired action, such as antibiotics, antifungals, antiinflammatories, or antiviral compounds. The active agent can comprise two or more isoflavones or derivatives thereof in combination or synergistic mixture. The active compounds can also be administered with lipid lowering agents such as probucol and nicotinic acid; platelet aggregation inhibitors such as aspirin; antithrombotic agents such as coumadin; calcium channel blockers such as verapamil, diltiazem, and nifedipine; angiotensin converting enzyme (ACE) inhibitors such as captopril and enalapril, and β-blockers such as propanolol, terbutalol, and labetalol. The compounds can also be administered in combination with nonsteriodal antiinflammatories such as ibuprofen, indomethacin, aspirin, fenoprofen, mefenamic acid, flufenamic acid and sulindac. The compounds can also be administered with corticosteroids.

The co-administration may be simultaneous or sequential. Simultaneous administration may be effected by the compounds being in the same unit dose, or in individual and discrete unit doses administered at the same or similar time. Sequential administration may be in any order as required and typically will require an ongoing physiological effect of the first or initial active agent to be current when the second or later active agent is administered, especially where a cumulative or synergistic effect is desired.

The isoflavones of formula (I) for use in the present invention may be derived from any number of sources readily identifiable to a person skilled in the art. Preferably, they are obtained in the form of concentrates or extracts from plant sources. Again, those skilled in the art will readily be able to identify suitable plant species, however, for example, plants of particular use in the invention include leguminous plants. More preferably, the isoflavone extract is obtained from chickpea, lentils, beans, red clover or subterranean clover species and the like.

Isoflavone extracts may be prepared by any number of techniques known in the art. For example, suitable isoflavone extracts may be prepared by water/organic solvent extraction from the plant source. It will be appreciated that an isoflavone extract may be prepared from any single tissue of a single species of plant or a combination of two or more different tissues thereof. Similarly, an extract may be prepared from a starting material which contains a heterogeneous mixture of tissues from two or more different species of plant.

Generally, where an isoflavone extract is prepared from plant material, the material may be comminuted or chopped into smaller pieces, partially commuted or chopped into smaller pieces and contacted with water and an organic solvent, such as a water miscible organic solvent. Alternatively, the plant material is contacted with water and an organic solvent without any pre-treatment. The ratio of water to organic solvent may be generally in the range of 1:10 to 10:1 and may, for example, comprise equal proportions of water and solvent, or from 1% to 30% (v/v) organic solvent. Any organic solvent or a mixture of such solvents may be used. The organic solvent may preferably be a C2-10, more preferably a C1-4 organic solvent (such as methanol, chloroform, ethanol, propanol, propylene glycol, erythrite, butanol, butanediol, acetonitrile, ethylene glycol, ethyl acetate, glycidol, glycerol dihydroxyacetone or acetone). Optionally the water/organic solvent mixture may include an enzyme which cleaves isoflavone glycosides to the aglycone form. The mixture may be vigorously agitated so as to form an emulsion. The temperature of the mix may range, for example, from an ambient temperature to boiling temperature.

Exposure time may be between one hour to several weeks. One convenient extraction period is twenty-four hours at 90° C. The extract may be separated from undissolved plant material and the organic solvent removed, such as by distillation, rotary evaporation, or other standard procedures for solvent removal. The resultant extract containing water soluble and non-water soluble components may be dried to give an isoflavone-containing extract, which may be formulated with one or more pharmaceutically acceptable carriers, excipients and/or auxiliaries according to the invention.

An extract made according to the description provided in the previous paragraphs may contain small amounts of oil which include isoflavones in their aglycone form (referred to herein as isoflavones). This isoflavone enriched oil, may be subject to HPLC to adjust the isoflavone ratios, or, if it is at the desired isoflavone ratio, may be dried, for example in the presence of silica, and be formulated with one or more carriers, excipients and/or auxiliaries to give an isoflavone containing extract. Alternatively, the isoflavones contained in said small amounts of oil may be further concentrated by addition to the oil of a non-water soluble organic solvent such as hexane, heptane, octane acetone or a mixture of one or more of such solvents. One example is 80% hexane, 20% acetone w/w having high solubility for oils but low solubility for isoflavones. The oil readily partitions into the organic solvent, and an enriched isoflavone containing extract falls out of solution. The recovered extract may be dried, for example in an oven at 50° C. to about 120° C., and formulated with one or more pharmaceutically acceptable carriers, excipients and/or auxiliaries.

It will be appreciated that the present invention also contemplates the production of suitable isoflavones, functional derivatives, equivalents or analogues thereof, by established synthetic techniques well known in the art. See, for example, Chang et al. (1994) which discloses methods appropriate for the synthesis of various isoflavones.

International Patent Applications WO 98/08503 and WO 00/49009 (which are incorporated herein in their entirety by reference) and references cited therein also provide general synthetic methods for the preparation of isoflavonoid compounds for use in the present invention.

General methods known in the art may also be employed by those skilled in the art of chemical synthesis for constructing the platinum complexes depicted in formula (I), and by reference to the general schemes 1 and 2 below.

Chemical functional group protection, deprotection, synthons and other techniques known to those skilled in the art may be used where appropriate in the synthesis of the compounds of the present invention.

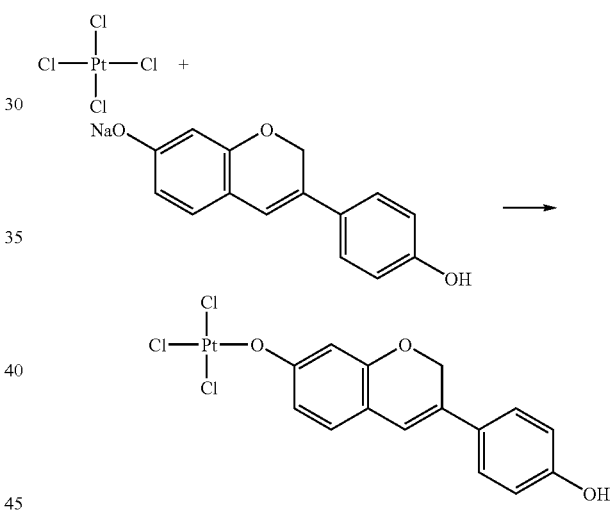

Scheme 1

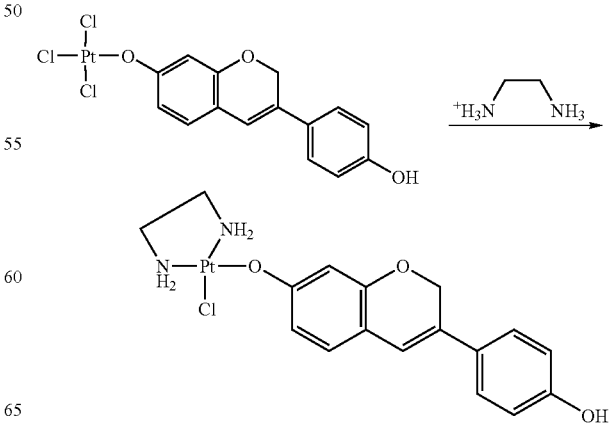

Scheme 2

The inventors have found a surprising synergy between the compounds of formula (I), and in particular the isoflav-3-ene compounds of formula (VIa), with known chemotherapeutic agents. The isoflavonoid compounds of the invention are found to restore or at least improve chemosensitivity to previously resistant cancer cell lines. In particular, dehydroequol (12, DHE) is found to exhibit synergistic interaction with cisplatin, carboplatin and paclitaxel with various established cancer cell lines, in particular the ovarian cancer cell lines Cp70 and A27A0. Synergism was also observed with prostate cancer cell lines DU145 and PC3 and pancreatic cell line HPAC.

These results are further elucidated in the examples which follow. These results show that combination chemotherapy with the isoflavonoid compounds with established anticancer agents are useful in the treatment of proliferation of cancer cells and neoplastic tumours by reducing the $IC_{50}$ of standard chemotherapy. Administration of the isoflavonoid compounds described herein either simultaneously, sequentially or as a pre-treatment to standard chemotherapies increases the sensitivity of the cancer cells and tumours to chemotoxic agents.

The Examples show the efficacy of combination chemotherapy with dehydroequol as a treatment for epithelial ovarian cancer cells by such reduction of the IC50 of standard chemotherapy. This thereby increases sensitivity of the cancer cells to chemotoxic agents. The results of these tests and trial are important as ovarian cancer is the fourth leading cause of cancer death and the most lethal of the gynaecologic malignancies. Recent new therapies have led to some improvement in the five year survival, yet there has been no improvement in the overall survival. The main limitations of therapy in ovarian cancer patients are chemoresistance and side-effects. The combination chemotherapy and isoflavonoid pre-treatment addresses the survival rates of patients undergoing the chemotherapy, and in particular those patients with ovarian cancer. Without wishing to be limited to theory, it is believed that the isoflavone derivative dehydroequol induces apoptosis in ovarian cancer cells by specifically removing the blockers of apoptosis.

The invention is further described with reference to the following non-limiting examples.

Example 1

Dehydroequol-Cisplatin Synergy In Vitro

The effect of a composition comprising the platinum complex cisplatin and the isoflavonoid compound dehydroequol (compound No. 12) on various cancer cell lines was assessed on culture plates. Cell viability was determined using CellTiter©. Apoptosis was evaluated using Hoechst 33342 dye.

It was found that the amount of cisplatin needed to kill a set number of cancer cells is less when in admixture with an isoflavonoid compound as compared to a control with cisplatin alone. This example demonstrates the surprising synergy between cisplatin and the isoflavonoid compounds of the present invention. Dehydroequol was found to exhibit a strong synergistic interaction with cisplatin in cell lines derived from ovarian (A2780, Cp70), prostate (DU145 and PC3) and pancreatic (HPAC) cancers. Table 1 below shows that the $IC_{50}$ of cisplatin against the mentioned cell lines is markedly lowered by co-incubating representative cells with a sub-$IC_{50}$ level (2 µM) of dehydroequol.

TABLE 1

Effect of concurrent exposure to dehydroequol and cisplatin on the $IC_{50}$ levels on nominated cancer cell lines

| Cell line | $IC_{50}$ (uM) | | Cisplatin $IC_{50}$ (uM) |
|---|---|---|---|
| | Cisplatin | dehydroequol | +2 uM dehydroequol |
| A2780 | 3.0 | 1.7 | <0.001 |
| CP70 | 10.4 | 1.5 | 0.1 |
| HPAC | 34.5 | 50.0 | 7.7 |
| PC3 | 0.4 | 9.6 | <0.001 |
| DU145 | 5.0 | 5.9 | 0.1 |

Example 2

Dehydroequol-Cisplatin, Dehydroequol-Carboplatin and Dehydroequol-Paclitaxel Synergy In Vitro and In Vivo Methods The in vitro studies were performed using ovarian cancer cells isolated from ascites using an immunomagnetic assay and established ovarian cancer cell lines CP70 and A2780. Cell viability was determined using CellTiter©. Apoptosis was evaluated using Hoechst 33342 dye. The in vivo effect was tested by injecting CP70 subcutaneously into nude mice. Animals received daily oral administration of dehydroequol, 10 or 20 mg/kg for 8 days alone or in combination with cisplatin 0.5 mg/kg. After 8 days the animals were sacrificed and the tumour volume was measured.

The IC50 for carboplatin ranged from 60 µg/ml to greater than 100 µg/ml (FIG. 1).

Figure 2:
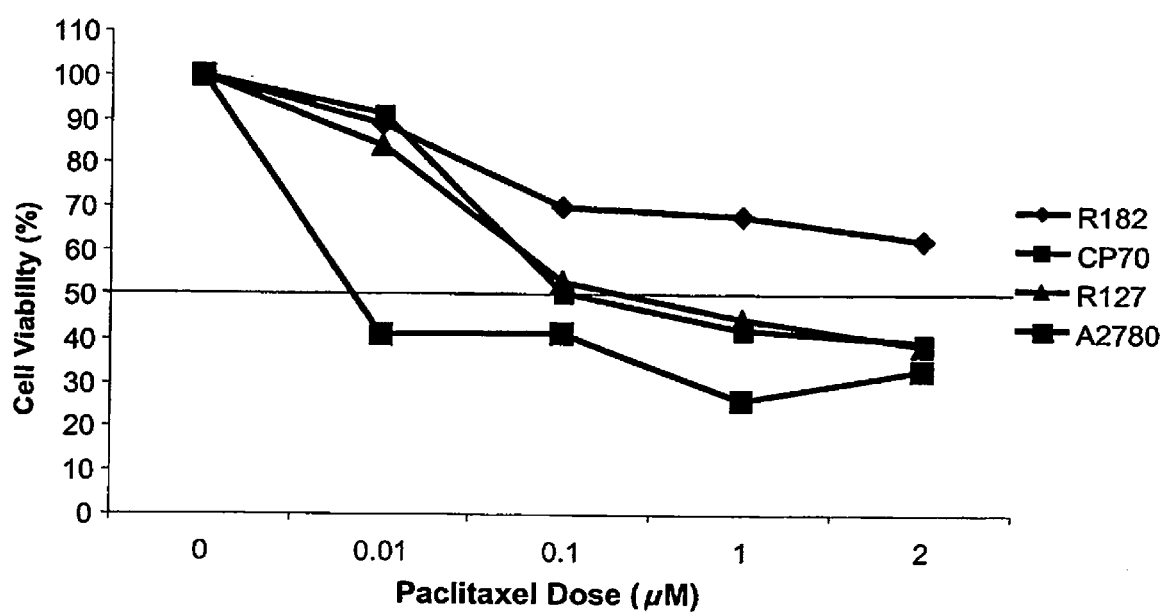
FIG. 2 represents the cell viability of various cancer cell lines over different concentrations of paclitaxel.

The IC50 for paclitaxel in the paclitaxel resistant cell line, R182, was greater than 2 µM (FIG. 2).

Figure 3:
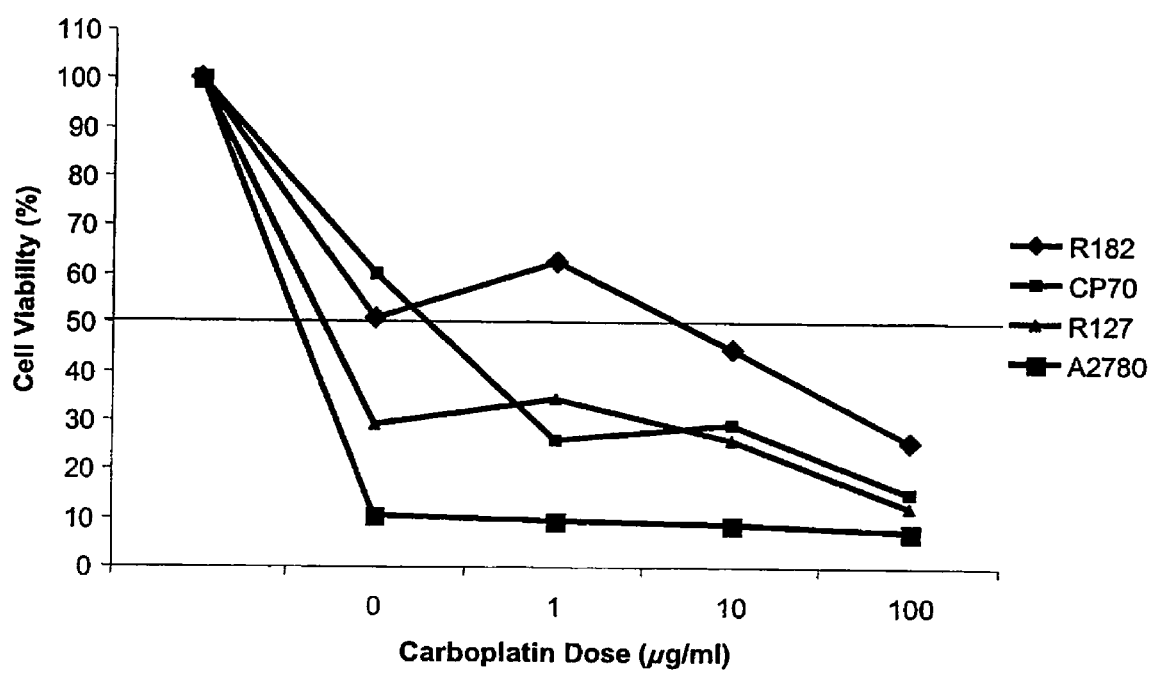
FIG. 3 represents the cell viability of various cancer cell lines over different concentrations of carboplatin following dehydroequol pre-treatment.
Figure 4:
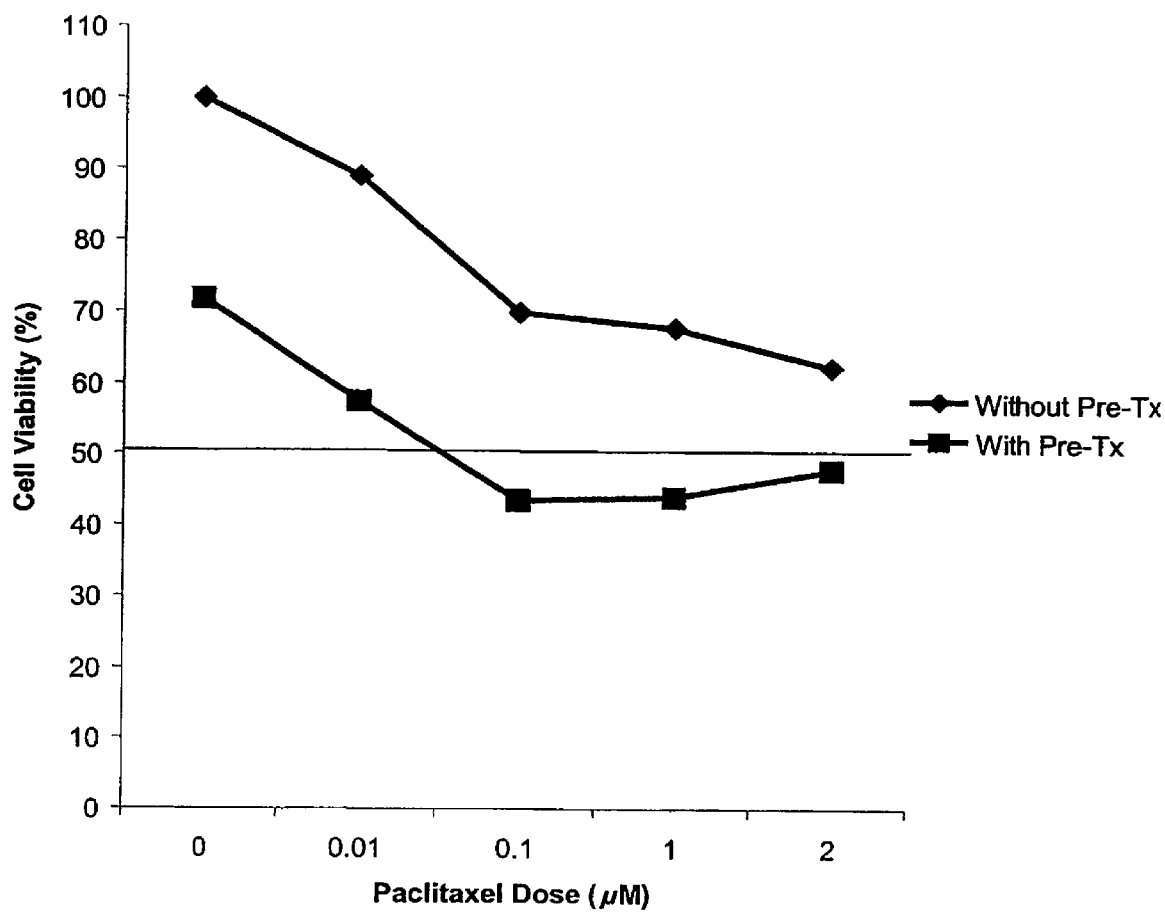
FIG. 4 represents the cell viability of various cancer cell lines over different concentrations of paclitaxel following dehydroequol pre-treatment.

Pre-treatment with dehydroequol (10 µg/ml) for two hours significantly reduced the IC50 for carboplatin (0.5 µg/ml+/− 0.5) and paclitaxel (0.05 µM) (FIGS. 3 and 4).

Figure 5:
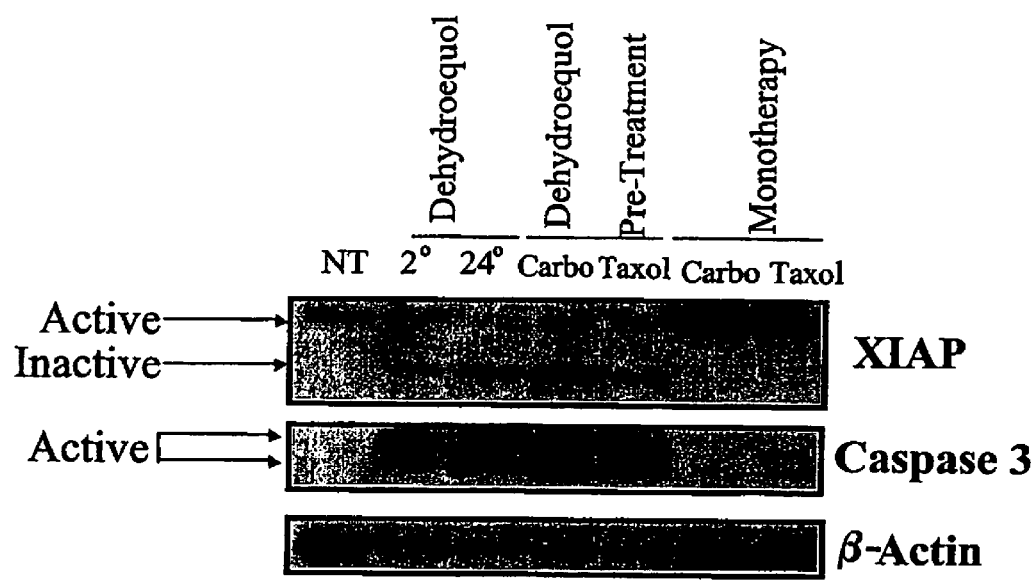
FIG. 5 represents a Western Blot analysis of carboplatin or paclitaxel treatment resistant ovarian cancer CP70 cells with and without dehydroequol pre-treatment.

Western blot analysis demonstrated that resistant ovarian cancer cells expressed high levels of active XIAP. Additionally, the active form of caspase 3 in chemoresistant cells was not detected. Caspase 3 activation was observed in the chemoresistant cells only after pre-treatment with dehydroequol (FIG. 5).

Figure 6:
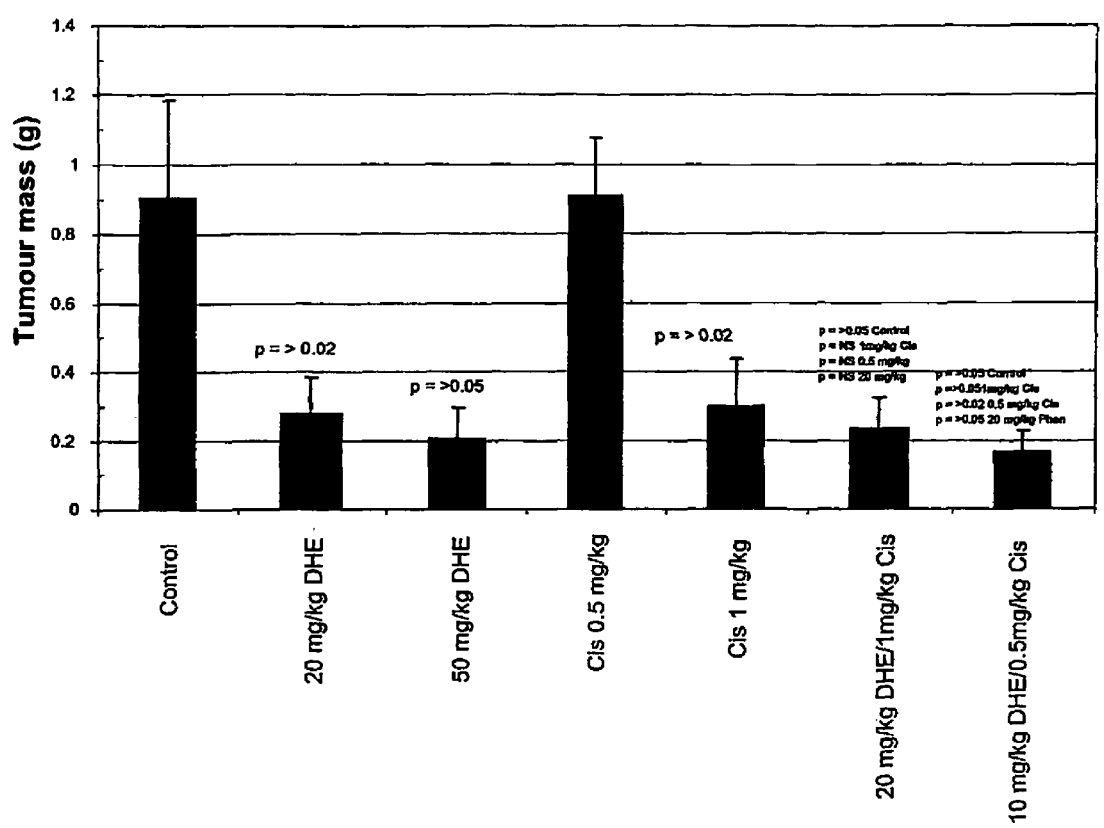
FIG. 6 represents tumour mass comparison of dehydrequol and cisplatin when delivered as single active agents or combination therapy with the 5% HPBCD vehicle control group.
Figure 7:
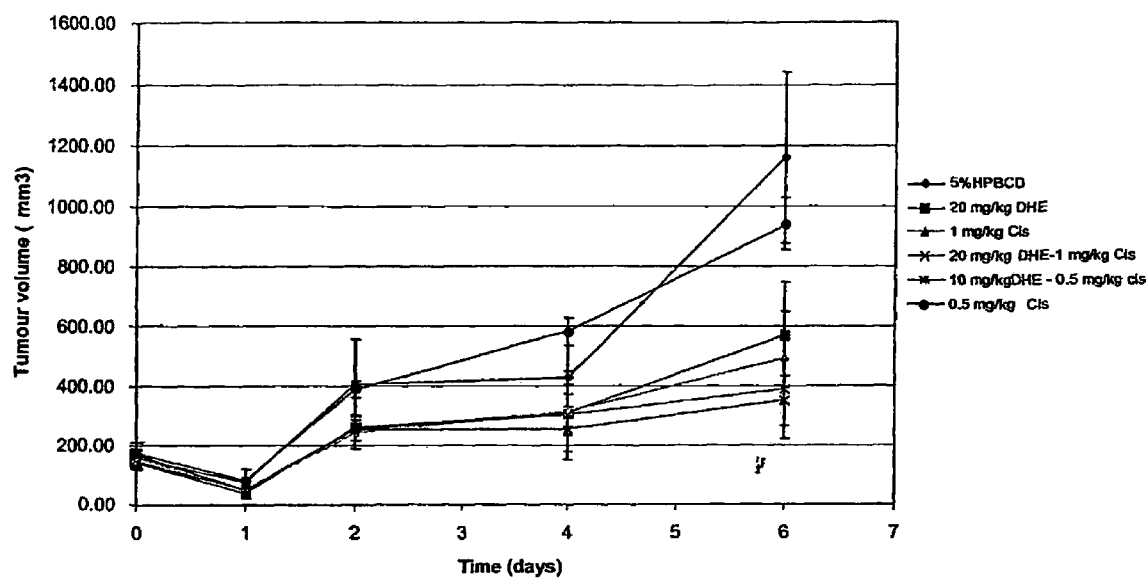
FIG. 7 represents tumour volume comparison of dehydrequol and cisplatin when delivered as single active agents or combination therapy with the 5% HPBCD vehicle control group.

FIGS. 6 and 7 depict the results of the next study, where 20 mg/kg dehydroequol (DHE) 5% HPBCD was compared to delivery of cisplatin and to a combination of dehydroequol and cisplatin. The 20 mg/kg Phen-1 mg/kg cisplatin dosage regimen inhibited tumour proliferation but the data was not significantly different from cisplatin (1 mg/kg) and dehydroequol (20 mg/kg) controls. Importantly and somewhat surprisingly, the lower dose 10 mg/kg dehydroequol-0.5 mg/kg cisplatin combination regimen inhibited tumour proliferation more markedly than that over the 20 mg/kg dehydroequol-1 mg/kg cisplatin (% T/C=14.7) regimen and the data were significantly different from single agent controls (FIGS. 6 and 7).

Dehydroequol treatment for 48 hours (h) induced 60-80% decrease in cell viability in carboplatin and paclitaxel resistant cells. Pre-treatment with DHE alone for 2 h decreased cell viability by 20%. Furthermore, pre-treatment (2 h) with DHE in chemoresistant cells followed by carboplatin or paclitaxel for 48 h resulted in a 30% and 50% significant decrease in cell viability, respectively. Hoechst stain confirmed the presence of apoptosis in the treated cells. In vivo, cisplatin (0.5 mg/kg) had no effect on tumour size while the combination of DHE (10 mg/kg) and cisplatin 0.5 mg/kg) reduced tumour mass by 75% (p=0.05).

Example 3

Toxicity—Dehydroequol and Cisplatin

Figure 8:
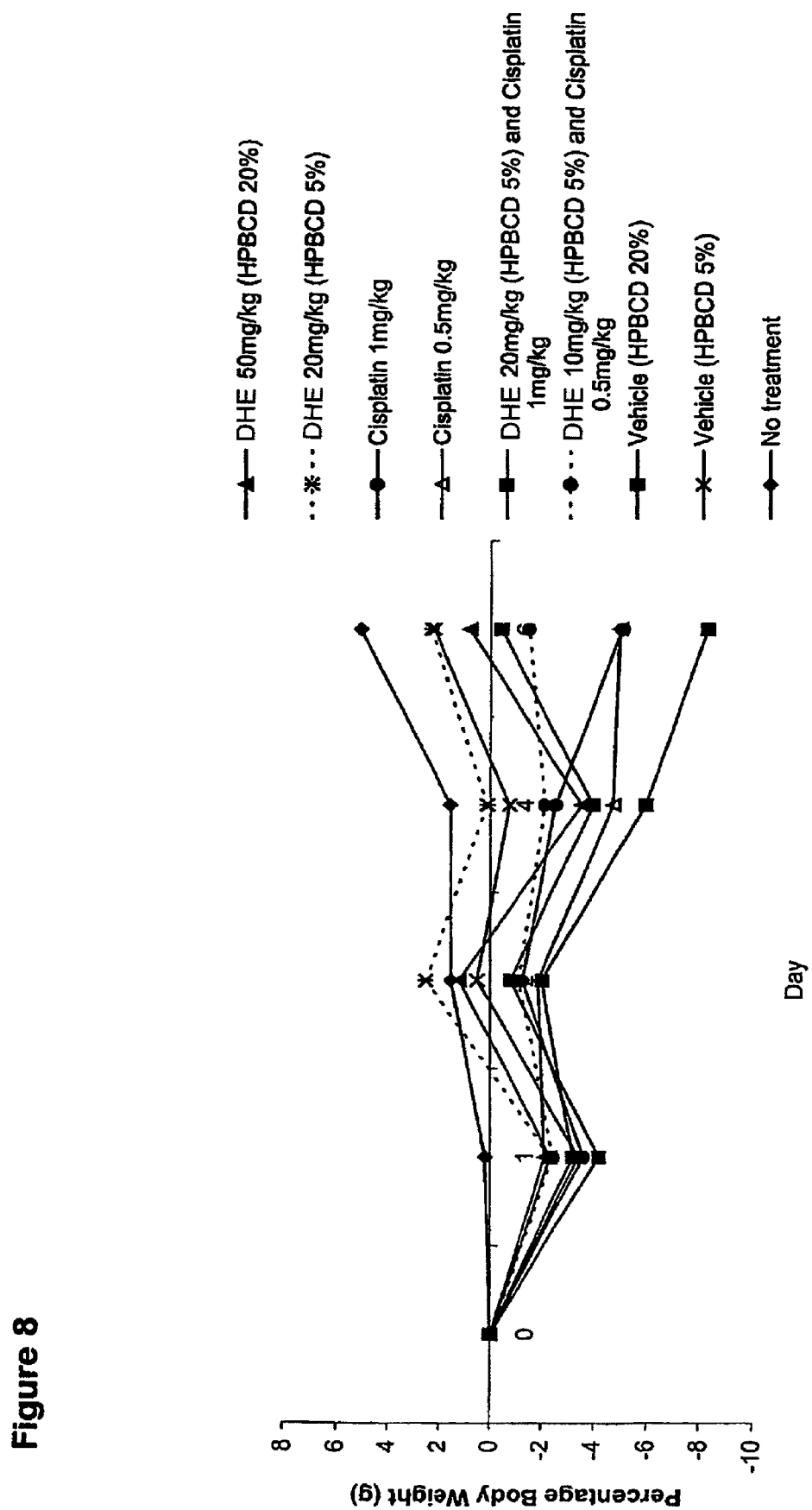
FIG. 8 represents a body weight comparison as an indicator of toxicity in each dehydroequol, cisplatin or combination treatment group in comparison with the HPBCD 5% vehicle control.

No overt signs of toxicity were noted at any of the dosage regimens used as shown in FIG. 8. Fluctuations in body mass were within ethically acceptable boundaries.

These examples highlight the utility of the isoflavonoid compounds of formula (I) in combination with chemotherapeutic agents, and the compounds of formula (II) or (IIa) and (I) as therapeutic agents for inducing sensitivity to chemoresistant cancer cells and tumours to low levels of chemotherapy and to the general down regulation of cell proliferation and the treatment, amelioration, defence against, prophylaxis and/or prevention of the therapeutic indications.

Those skilled in the art will appreciate that the invention described herein is susceptible to variations and modifications other than those specifically described. It is to be understood that the invention includes all such variations and modifications. The inventions also includes all of the steps, features, compositions and compounds referred to or indicated in the specification, individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

The invention claimed is:

1. A method of increasing the sensitivity of cancer cells or a tumour to a chemotherapeutic agent by contacting said cells or tumour with an isoflavonoid compound of formula 12:

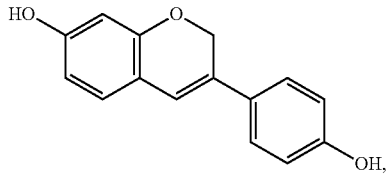

wherein
(a) the cancer or tumor is ovarian, pancreatic or prostate cancer or tumor, and the chemotherapeutic agent is cisplatin, or
(b) the cancer or tumor is ovarian cancer or tumor, and the chemotherapeutic agent is carboplatin, or
(c) the cancer or tumor is ovarian or prostate cancer or tumor, and the chemotherapeutic agent is paclitaxel, or
(d) the cancer or tumor is ovarian or pancreatic cancer or tumor, and the chemotherapeutic agent is gemcitabme or doxorubicin.

2. A method of claim 1, wherein prior to the contacting, the cancer cells or tumour were/was not sensitive to the chemotherapeutic agent.

3. A method of claim 1, wherein the compound of formula 12 is administered to a subject in need of such treatment.

4. A method comprising administering to a subject having cancer a therapeutically effective amount of a compound of formula 12 and a chemotherapeutic agent:

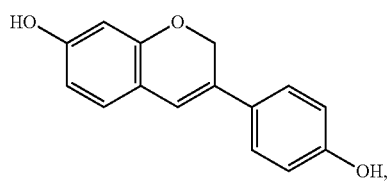

wherein
(a) the cancer is ovarian, pancreatic or prostate cancer, and the chemotherapeutic agent is cisplatin, or
(b) the cancer is ovarian cancer, and the chemotherapeutic agent is carboplatin, or
(c) the cancer is ovarian or prostate cancer, and the chemotherapeutic agent is paclitaxel, or
(d) the cancer is ovarian or pancreatic cancer, and the chemotherapeutic agent is gemcitabine or doxorubicin.

5. A method of claim 4, wherein the administration of the compound of formula 12 precedes the administration of the chemotherapeutic agent.

6. A method of claim 4, wherein the administration of the compound of formula 12 and the chemotherapeutic agent is simultaneous.

7. A method of claim 4, wherein the combination cancer therapy follows observed resistance by cancer cells or tumour to the chemotherapeutic agent.

* * * * *